United States Patent [19]

Mers Kelly

[11] Patent Number: 5,540,237
[45] Date of Patent: Jul. 30, 1996

[54] BODY TISSUE SUSPENSION DEVICE

[75] Inventor: William C. Mers Kelly, Xenia, Ohio

[73] Assignee: Louisville Laboratories, Inc., Louisville, Ky.

[21] Appl. No.: 317,134

[22] Filed: Oct. 3, 1994

Related U.S. Application Data

[63] Continuation-in-part of Ser. No. 86,010, Jul. 11, 1993, Pat. No. 5,352,211.

[51] Int. Cl.⁶ .............................. A61G 15/00; A61F 5/37; A61B 19/00
[52] U.S. Cl. ........................ 128/845; 128/846; 128/869
[58] Field of Search .................................. 128/845, 846, 128/DIG. 20; 606/86, 87, 88, 96, 97, 98; 623/16, 17, 23

[56] References Cited

U.S. PATENT DOCUMENTS

| | | | |
|---|---|---|---|
| 2,493,598 | 1/1950 | Rozek | 128/20 |
| 2,586,488 | 2/1952 | Smith | 128/20 |
| 2,845,925 | 8/1958 | Jayle | 128/20 |
| 3,038,468 | 6/1962 | Raeuchle | 128/20 |
| 3,762,401 | 10/1973 | Tupper | 128/20 |
| 3,823,709 | 7/1974 | McGuire | 128/850 |

*Primary Examiner*—Michael A. Brown
*Attorney, Agent, or Firm*—Don Halgren

[57] ABSTRACT

The present invention includes a support arm arrangement which is disposed over a patient being operated upon. The support arms are placed in holes in a block or pad on which the patient is lying. Adhesive coated securement pads are attached to the support arms and are also secured by adhesive to the skin of the patient to lift and thereby expand portions of a body cavity being operated upon.

9 Claims, 5 Drawing Sheets

BODY TISSUE SUSPENSION DEVICE

This application is a continuation-in-part of my U.S. patent application Ser. No. 08/086,010, filed 07/11/93, now U.S. Pat. No. 5,352,211 which is incorporated herein by reference in its entirety.

BACKGROUND OF THE INVENTION

1. Field of the Invention

This invention relates to devices for holding body tissue, and more particularly to a body tissue support arrangement acting from the outside of the body being operated upon.

2. Prior Art

Surgery in a body cavity or void is a very common experience. Modern surgery is often done laproscopically in the abdomin or in thorasic surgery.

Current surgical practices utilize the use of carbon dioxide to inflate the body cavities during laproscopic surgery. Typically carbon dioxide is directed into the body cavity through a body opening utilizing a lumen therethrough. This permits the chest and stomach walls to be expanded to permit a surgeon to operate with his laproscopic devices therewithin. A drawback of this type of operation, wherein carbon dioxide is utilized under pressure, is that the carbon dioxide could be driven into the tissue of the body and cause ischemia, which is an inflammation of the tissue if such pressure of the carbon dioxide were to last more than one hour within the body. Also, when laproscopic instruments are utilized within a pressurized cavity, leakage may occur. With laproscopic devices, since pressure is utilized within the body, the instruments may often require valves to prevent or minimize any backflow or leakage from the instrument.

It is an object of the present invention, to minimize the need for any inflation gases within a body cavity during laproscopic surgery therein.

It is a further object of the present invention to avoid the requirement that the standard surgical instruments utilize valves therewith.

It is a yet further object of the present invention, to prevent the formation of carbolic acid inside the patient being operated upon by virtue of the carbon dioxide pressurized within the patient.

BRIEF SUMMARY OF THE INVENTION

The present invention comprises a tissue support apparatus which permits a body cavity such as the abdomen or chest of a patient, to be supported in a lifted configuration so as to maximize a void or space within that body cavity during surgery therein. The present apparatus may include a planar pad on which the patient being operated upon, is disposed. The pad has a plurality of cell-like holes spaced thereacross. The patient is placed on top of the planar pad, the spaced holes being exposed under and to both the left and right sides of the patient thereon. A suspension means is arranged across any pair of those holes on opposite sides of the pad, which is also on opposite sides of the patient that is the left or the right side thereof. The suspension means has a tissue engaging securement means arranged therewith to engage the tissue or skin of the patient and to thereby suspend the wall of the abdomen or stomach, or body cavity therefrom.

The suspension means in a preferred embodiment thereof, may include an elongated metal or plastic rod, having two ends, each end mating in the cell-like hole one on the left and one on the right on the pad on which the patient is lying. A pair of these suspension rods may also be juxtaposed in an "X" shaped pattern across the patient or they may be arranged in a parallel disposition across the chest, abdomen or stomach of the patient lying thereunder.

The securement means which is disposed on the securement rods and is also attached to the tissue or skin of the patient, may comprise in a first embodiment, one or more elongated planar strips. Each strip would have an upper surface having an elongated clevis arrangement longitudinally disposed therealong. The clevis would have a bore therethrough, the bore being arranged to receive the suspension rod therethrough. On the lower side of the pad, a mildly aggressive adhesive would be disposed. The adhesive would be placed against the skin once the pad was loaded onto a suspension rod. Each end of the suspension rod would be placed within a hole on opposite sides of the patient who is on the pad. The suspension rod would form a curvilinear suspension arm from which the abdomen, stomach, chest or other tissue wall was being supported. These elongated adhesive pads on the suspension rods, could be suspended across the patient in parallel form so as to permit an operating area to occur therebetween, or those suspension rods could be disposed in any other manner such as an "X" shaped or crisscrossing in order to leave one area open more than another on the abdomen of the patient. It is also to be noted, that by using securement pads of a particular shorter length, placed over discrete areas of the patient's body cavity to be suspended, that the body cavity could be expanded in a desired direction. That is, the abdomen wall, stomach wall or chest could have only a particular area over which an operation was occuring to be moved and pulled away further than the other side of the patient's cavity being operated upon, thus permitting expansion of a body cavity into a particular desired shape, contortion or direction.

In a yet further embodiment of the present invention, the suspension could include a round, square or triangular shaped pad of planar configuration, having a lowermost surface with an adhesive thereon and an uppermost surface which has a plurality of projecting flexible legs extending upwardly therefrom. Each pad could be round, square, oval or elongated, to conform to certain suspension requirements. Each pad preferrably has a central opening disposed through its planar base portion. Each leg from base of the pad would have an upper or distalmost end which would anchor in a receiving block. The flexible pad legs would be secured to the lower periphery of the support block. The support block would have a bore extending transversely therethrough. The bore would be arranged to receive the support rod which extends in an arcuate manner across the patient from one side to the other, as in the aforesaid embodiment. This type of pad also permits directional expansion of the body cavity while it also permits access of some surgical device through the aforementioned central opening in the pad base.

The invention comprises a body tissue suspension device for supporting the body wall of a patient undergoing an operation within that body wall, the device comprising: a lowermost block on which the patient being operated upon is disposed; a support arm arranged with respect to the block and over at least a portion of the patient; securement means attached to the support arm and to the patient, so as to provide suspension of the body wall of the patient during a medical procedure thereon. The block has a plurality of holes therein, and the support arm is matable in at least one of the holes to hold up tissue being supported thereunder.

The securement means comprises a pad having an interlocking arrangement for attachment to the support arm. The pad has a lower surface with a layer of adhesive thereon for securement to the skin of a patient being operated upon. The securement means can be located selectively on the support arm to provide selective directional expansion of a body cavity during a surgical operation, by pulling on the body wall in a desired eccentric direction. The securement means has a planar base portion, the planar base portion having a central opening therethrough. The pad is an elongated extruded polymer having an upper surface with an elongated clevis thereon, the clevis having an elongated bore therethrough for receipt of the support arm. The support arm may comprise a metal rod of generally rigid yet bendable construction, to permit it to be arcuately disposed over the patient, yet support the securement means and tissue body wall therebeneath. The metal rod has an end which is receivable and supported in at least one hole in the lowermost block under the patient.

The invention also comprises a method for supporting a body wall of a patient, comprising the steps of: arranging a lowermost block adjacent the patient being operated upon; securing a support arm from the block; attaching a securement means to the support arm; and attaching the securement means to the patient so as to support a body wall thereof; arranging the securement means on a pair of support arms which extend across the body of the patient: arranging the support arms parallel to one another across the body of the patient; inserting a medical device through a central opening in a base portion of said securement means; and energyzing the lowermost block so as to permit it to function as an electrode in conjunction with an electrical medical device utilized on the patient.

BRIEF DESCRIPTION OF THE DRAWINGS

The objects and advantages of the present invention will become more apparent, when viewed in conjunction with the following drawings, in which.

DESCRIPTION OF THE PREFERRED EMBODIMENT

Figure 1:
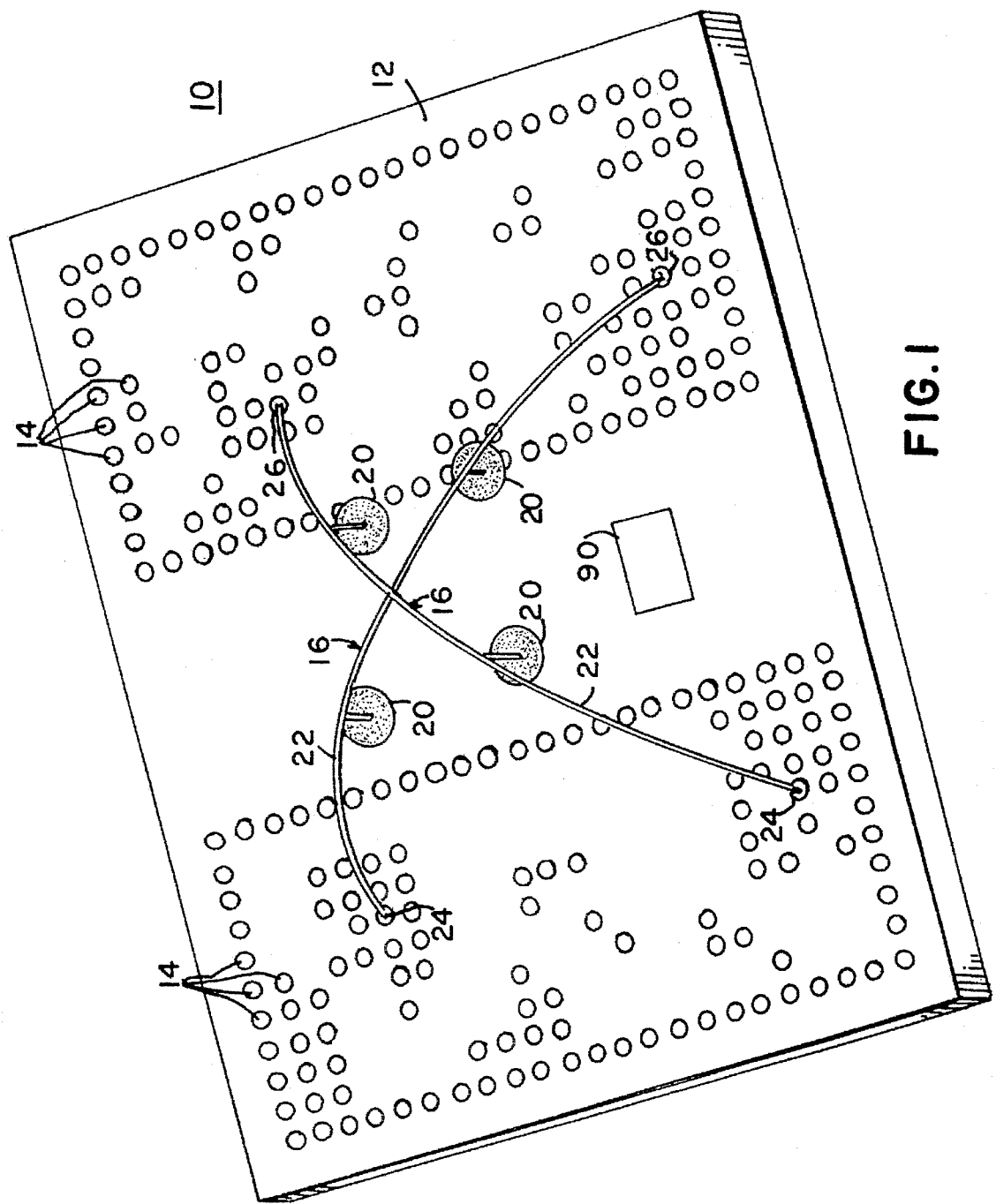
FIG. 1 is a perspective view of a block or pad and suspension arrangement constructed according to the principles of the present invention.

Referring to the drawings in detail, and particularly to FIG. 1, there is shown the present invention which is a tissue support apparatus 10 which permits a body cavity such as the abdomen or chest of a patient, to be supported in a lifted configuration so as to maximize a void or space within that body cavity during surgery therein. The present tissue support apparatus 10 may comprise a planar block or pad 12 on which the patient being operated upon, is disposed. The block or pad 12 has a plurality of cell-like holes 14 about 0.125 to about 0.25 inches in diameter, spaced across the upper surface of the pad 12 in a rectilinear pattern. The pad 12 is preferably made from a firm layer of polymer or hard rubber, the holes 14 being rigid and unyielding enough so as to not distort easily. The patient "P" is placed on top of the planar pad 12, the spaced holes 14 being exposed under and to the left and right sides of the patient "P" thereon. A suspension means 16 is arranged across a pair of those holes 14 on opposite sides of the pad 12 being also on opposite sides of the patient, that is, the left or the right side thereof. The suspension means 16 has a tissue engaging securement means 20 arranged therewith to engage the tissue or skin of the patient "P" and to thereby suspend the wall of the abdomen or stomach, or body cavity therefrom.

The suspension means 16 in a preferred embodiment thereof, may include an elongated metal or plastic rod 22, of about 0.125 to about 0.25 inches in diameter, having two ends 24 and 26, each end 24 and 26 mating in one of the hole 14 on the left and one on the right on the pad 12 on which the patient is lying. A pair of these suspension rods 22 may be juxtaposed in an "X" shaped pattern across the patient or they may be arranged parallel to one another across the chest, abdomen or stomach of the patient lying thereunder.

Figure 3:
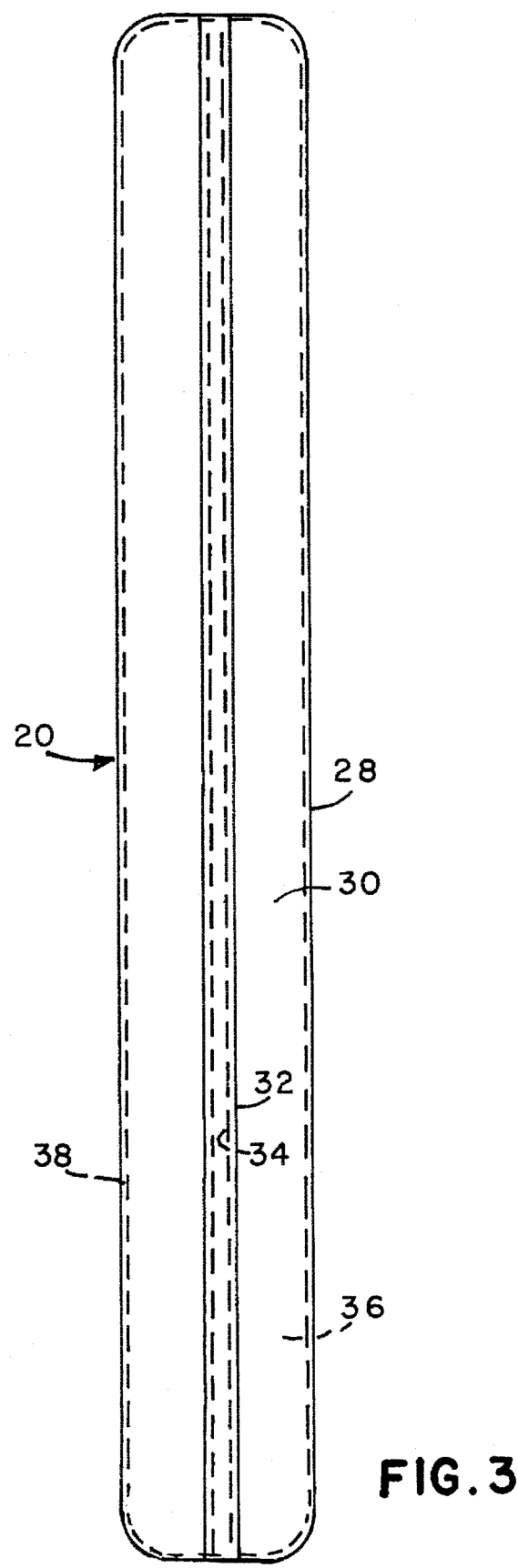
FIG. 3 is a plan view of an elongated pad through which a suspension rod of the present invention mates.
Figure 4:
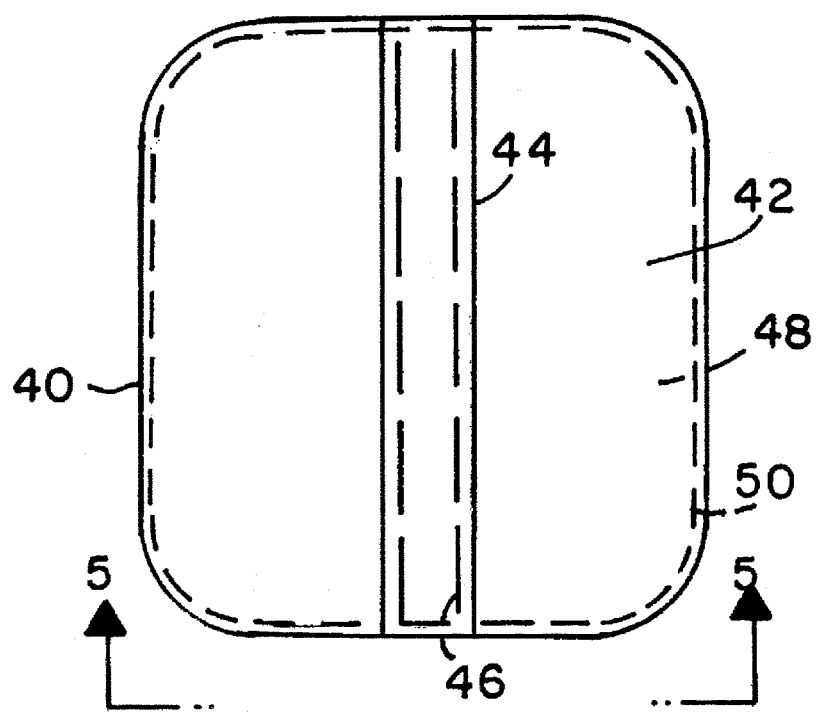
FIG. 4 is a view of a short pad, otherwise similar to the pad shown in FIG. 3.
Figure 5:
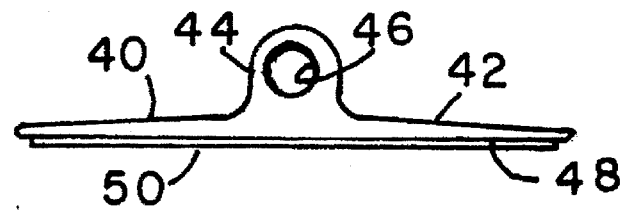
FIG. 5 is a view taken along the line V—V of FIG. 3.

The securement means 20 which is disposed on the suspension rods 22 and is also attached to the tissue or skin of the patient, may, as shown in FIG. 3, comprise in a first embodiment, one or more elongated planar strip pads 28. Each strip pad 28 would have an upper surface 30 having a clevis 32 arranged longitudinally therealong. The clevis 32 would have a bore 34 therethrough, the bore 34 arranged to receive the suspension rod 22 therethrough. Each strip pad 28 has a lower side 36 on which a mildly aggressive layer of adhesive 38 would be disposed. The layer of adhesive 38 would be placed against the skin once the strip pad 28 was loaded onto a suspension rod 22. Each end 24 and 26 of the suspension rod 22 would be placed within a hole 14 on opposite sides of the patient who is on the block 12. Each suspension rod 22 would form a curvilinear suspension arm from which tissue wall of the abdomen, stomach, chest or tissue wall was being supported. These elongated adhesive coated pads 28 on the suspension rods 22 could be suspended across the patient in parallel form (not shown) so as to permit an operating area to occur therebetween, or those suspension rods 22 could be disposed in any other manner such as an "X" shape or crisscrossing in order to leave one area open more than another on the abdomen of the patient. It is also to be noted, that by using a pad 40 of a particular shorter length (i.e. 1 to 4 inched long by about 1 to 2 inches wide), and placed over discrete desired areas of the patient's body cavity to be suspended, that that portion of the body cavity could be expanded in a desired direction. That is, the abdomen wall, stomach wall or chest could have its particular area over which an operation was occuring to be moved and pulled away further than is the other side of the patient's cavity being operated upon. The shorter adhesive coated pad 40, is typically made from an extrided polymer, and has an upper surface 42, a longitudinally extending clevis 44 with a receiving bore 46 therethrough. The shorter pad 40 has a lower surface 48 with a layer of adhesive 50 thereon, for permitting attachment of the pad 40 to the patient's skin. The short pad 40 is shown in an end view in FIG. 5.

Figure 2:
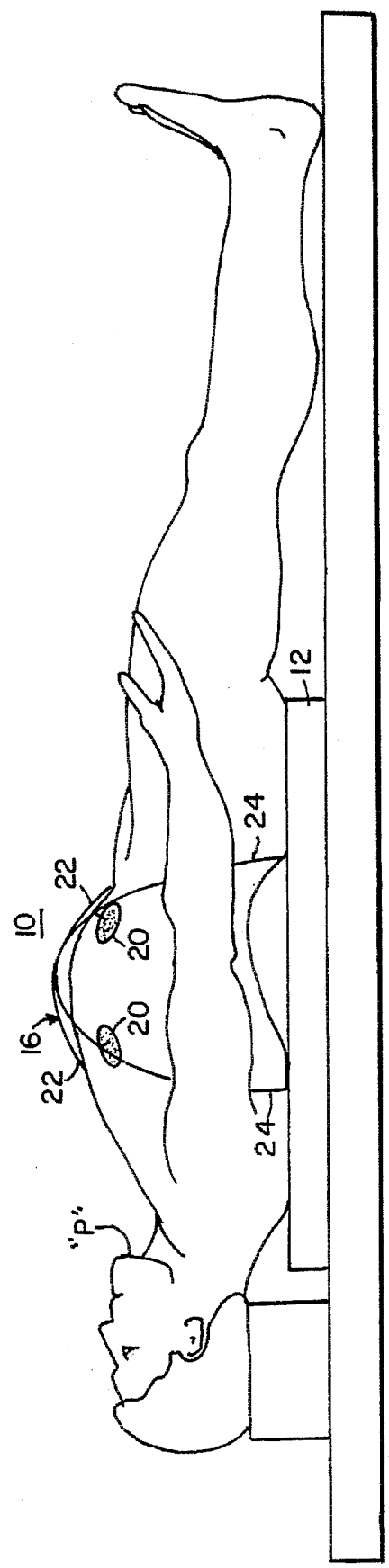
FIG. 2 is a side elevational view of a patient lying on the pad on an operating table with the suspension arrangement extending across the patient's abdomen.
Figure 6:
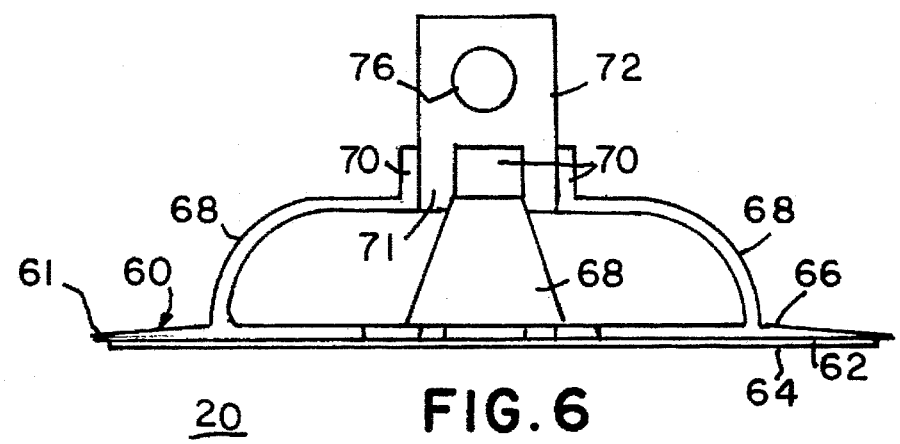
FIG. 6 is a side elevational view of a pad in a further embodiment thereof.
Figure 7:
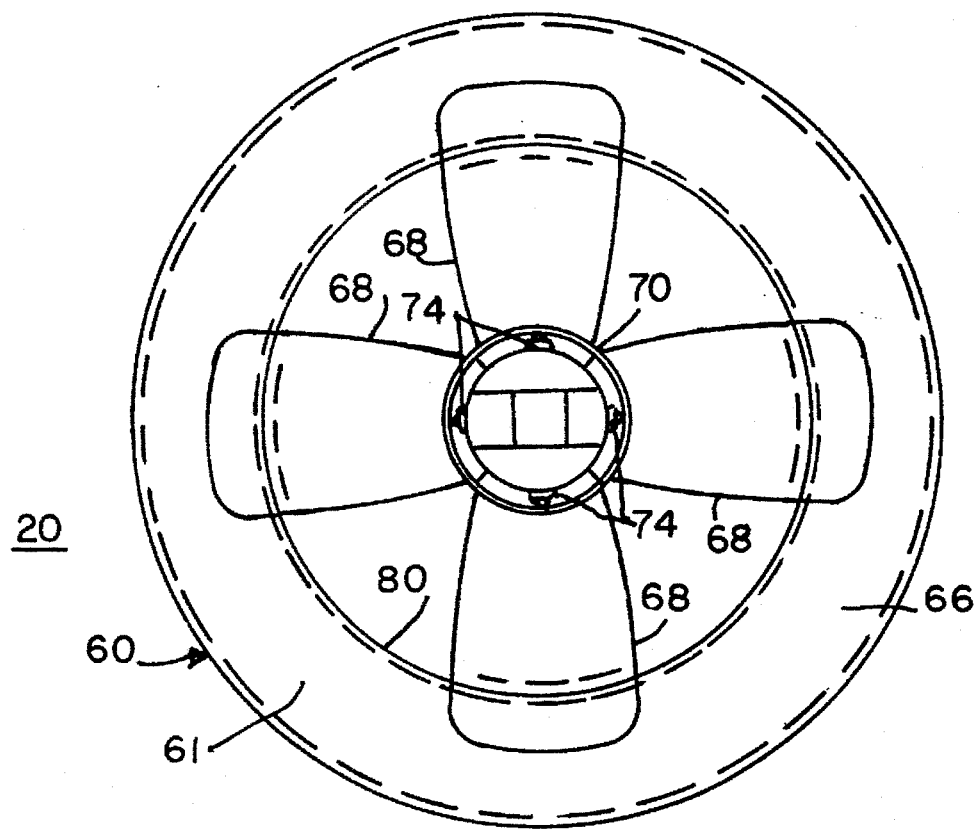
FIG. 7 is a plan view of the pad shown in FIG. 6.

In a yet further embodiment of the present invention, the suspension means 20 could include a round, square or triangular shaped "hanging" pad 60 of planar configuration, as shown in FIGS. 6 and 7, having a base 61 with a lowermost surface 62 with a layer of adhesive 64 thereon and an uppermost surface 66 which has a plurality of non-stretchable flexible legs 68 extending upwardly therefrom. Each leg 68, extending unitarily from the upper surface of the hanging pad 60, would have an upper or distalmost end 70 which would anchor in a receiving block 72 by a button or snap means in a manner similar to the connecting means at the distal end of the flexible legs shown in my co=pending application, cited above. The flexible legs 68 could be secured for example, by buttons 74 to the lower periphery 71 of the support block 72. The support block 72, preferrably made from a formed polymer, would have a bore 76 extending transversely therethrough, as shown in FIG. 6. The bore 76 would be arranged to receive support rod 22 which extends in an arcuate manner across the patient from one side to the other, as shown in FIGS. 1 and 2. This type of hanging pad 60 also permits directional expansion of the body cavity while also permitting access of some surgical device through the central opening in the pad base.

The hanging pad 60, shown as round in FIG. 7, but as mentioned hereinabove, could be of square, triangular, oval or other shape. The pad 60 in this embodiment, has a central opening 80 which permits access directly through a body being suspended and operated upon, yet also permits directional expandability of the cavity within the body wall being suspended by the pad 60. This hanging pad 60 could also be utilized to support organs within the body cavity during regular surgery, the base of the hanging pad 60 being arranged to wrap around the organ or member, there being no adhesive thereon but just a cradling by the base around that organ.

It is to be further noted, that the support block 72 at the upper end of the hanging pad 60, receives each support rod 22 through the transverse bore 76, which bore 76 is generally parallel to the plane of the base 61, could also have an opening thereadjacent, as embodied in my co-pending application, U.S. Ser. No. 08/086,010, incorporated herein by reference, and from which this continuation-in-part application springs, to simultaneously permit vertical access through the that block 72 between the distal ends of the legs 68 to hold a catheter, laparoscopic instrument or the like in a manner generally perpendicular to the base 61 of the "hanging" securement pad 60.

The block or pad 12 on which the patient is lying, may in still a further embodiment, be comprised of an electrode 90 in conjunction with a mono-polor electrical medical device being utilized within the patient being operated upon.

I claim:

1. A body tissue suspension device for supporting the body wall of a patient undergoing an operation within that body wall, said device comprising:

a lowermost block having a plurality of holes therein, the patient being operated upon being disposed on said block;

a support arm arranged with respect to said block and over at least a portion of the patient;

a body wall engaging securement means attached to said support arm and to the patient, so as to provide suspension of the body wall of the patient during a medical procedure thereon;

said support arm being matable in at least one of said holes in said block, to hold up tissue being supported thereunder;

said securement means comprising a pad having an interlocking arrangement for attachment to said support arm; and said pad having a lower surface with a layer of adhesive thereon for securement to the skin of a patient being operated upon.

2. A body tissue suspension device as recited in claim 1, wherein said securement means can be located selectively on said support arm to provide selective directional expansion of a body cavity during a surgical operation, by pulling on the body wall in a desired eccentric direction.

3. A body tissue suspension device as recited in claim 1, wherein said securement means has a planar base portion, said planar base portion having a central opening therethrough.

4. A body tissue suspension device as recited in claim 1, wherein said pad is an elongated extruded polymer having an upper surface with an elongated clevis thereon, said clevis having an elongated bore therethrough for receipt of said support arm.

5. A body tissue suspension device as recited in claim 1, wherein said support arm comprises a metal rod of generally rigid yet bendable construction, to permit it to be arcuately disposed over the patient, yet support the securement means and tissue body wall therebeneath.

6. A body tissue suspension device as recited in claim 5, wherein said metal rod has an end which is receivable and supported in at least one hole in said lowermost block under the patient.

7. A method for supporting a body wall of a patient, comprising the steps of:

arranging a lowermost block adjacent the patient being operated upon;

securing a support arm from said block;

attaching a tissue engaging securement means to said support arm;

attaching said securement means to the patient so as to support a body wall thereof;

arranging said securement means on an arrangement of support arm which extend across the body of the patient: and inserting a medical device through a central opening in a base portion of at least one of said tissue engaging securement means.

8. The method for supporting a body wall as recited in claim 7, including the step of:

arranging said support arms parallel to one another across the body of the patient.

9. The method for supporting a body wall as recited in claim 7, including the step of:

energyzing said lowermost block so as to permit it to function as an electrode in conjunction with an electrical medical device utilized on the patient.

* * * * *